United States Patent [19]

Lesher et al.

[11] 4,361,569

[45] Nov. 30, 1982

[54] 3-(HYDROXY OR HYDROXYMETHYL)-6-METHYL-5-(4-PYRIDINYL)-2(1H)-PYRIDINONE AND CARDIOTONIC USE THEREOF

[75] Inventors: George Y. Lesher, Schodack; Richard E. Philion, Sand Lake, both of N.Y.

[73] Assignee: Sterling Drug Inc., New York, N.Y.

[21] Appl. No.: 296,291

[22] Filed: Aug. 26, 1981

[51] Int. Cl.³ .................... A61K 31/44; C07D 213/69
[52] U.S. Cl. ..................................... 424/263; 546/257
[58] Field of Search .......................... 546/257; 424/263

[56] References Cited

U.S. PATENT DOCUMENTS 4,225,601 9/1981 Lesher et al. ..................... 546/257
4,297,360 10/1981 Lesher et al. ..................... 546/257
4,305,948 12/1981 Gruett et al. ..................... 546/257

*Primary Examiner*—Norma S. Milestone

*Attorney, Agent, or Firm*—Robert K. Bair; B. Woodrow Wyatt; Paul E. Dupont

[57] ABSTRACT

3-(Hydroxy or hydroxymethyl)-6-methyl-5-(4-pyridinyl)-2(1H)-pyridinone or pharmaceutically acceptable acid-addition salt thereof is useful as a cardiotonic agent. 3-Hydroxy-6-methyl-5-(4-pyridinyl)-2(1H)-pyridinone is prepared by autoclaving a mixture of a sodium or potassium lower-alkoxide, a lower-alkanol and 3-(chloro or bromo)-6-methyl-5-(4-pyridinyl)-2(1H)-pyridinone and acidifying the reaction mixture. 3-Hydroxymethyl-6-methyl-5-(4-pyridinyl)-2(1H)-pyridinone is prepared by reacting 6-methyl-5-(4-pyridinyl)-2(1H)-pyridinone with excess formaldehyde at an acidic pH. Said 3-(hydroxy or hydroxymethyl)-6-methyl-5-(4-pyridinyl)-2(1H)-pyridinone or pharmaceutically acceptable acid-addition salt thereof is disclosed as the active ingredient in cardiotonic compositions for increasing cardiac contractility and in the method for increasing cardiac contractility in a patient requiring such treatment.

7 Claims, No Drawings

3-(HYDROXY OR HYDROXYMETHYL)-6-METHYL-5-(4-PYRIDINYL)-2(1H)-PYRIDINONE AND CARDIOTONIC USE THEREOF

BACKGROUND OF THE INVENTION (a) Field of the Invention

This invention relates to 3-substituted-6-methyl-5-(4-pyridinyl)-2(1H)-pyridinones, useful as cardiotonic agents, and to their preparation.

(b) Description of the Prior Art

Lesher and Opalka U.S. Pat. No. 4,225,601, issued Sept. 30, 1980, shows 3-(hydroxy or hydroxymethyl)-5-(4-pyridinyl)-2(1H)-pyridinones to be useful as cardiotonic agents.

SUMMARY OF THE INVENTION

In a composition of matter aspect, the invention resides in the compound, 3-(hydroxy or hydroxymethyl)-6-methyl-5-(4-pyridinyl)-2(1H)-pyridinone or acid-addition salt thereof, useful as a cardiotonic agent.

In a process aspect the invention comprises autoclaving a mixture of an alkali metal alkoxide, a lower alkanol and 3-halo-6-methyl-5-(4-pyridinyl)-2(1H)-pyridinone and acidifying the reaction mixture to produce 3-hydroxy-6-methyl-5-(4-pyridinyl)-2(1H)-pyridinone.

In another process aspect the invention comprises reacting 6-methyl-5-(4-pyridinyl)-2(1H)-pyridinone with excess formaldehyde at an acidic pH to produce 3-hydroxymethyl-6-methyl-5-(4-pyridinyl)-2(1H)-pyridinone.

A composition aspect of the invention resides in a cardiotonic composition for increasing cardiac contractility, said composition comprising a pharmaceutically acceptable carrier and, as the active ingredient thereof, a cardiotonically effective amount of 3-(hydroxy or hydroxymethyl)-6-methyl-5-(4-pyridinyl)-2(1H)-pyridinone or pharmaceutically acceptable acid-addition salt thereof.

In a method aspect the invention relates to a method for increasing cardiac contractility in a patient requiring such treatment which comprises administering a medicament comprising a pharmaceutically acceptable carrier and, as the active component thereof, a cardiotonically effective amount of 3-(hydroxy or hydroxymethyl)-6-methyl-5-(4-pyridinyl)-2(1H)-pyridinone or pharmaceutically acceptable acid-addition salt thereof.

DETAILED DESCRIPTION INCLUSIVE OF PREFERRED EMBODIMENTS

In a composition of matter aspect the invention resides in 3-(hydroxy or hydroxymethyl)-6-methyl-5-(4-pyridinyl)-2(1H)-pyridinone or acid-addition salt thereof. These compounds are useful as cardiotonic agents, as determined by standard pharmacological evaluation procedures.

A process aspect of the invention resides in the process which comprises heating under pressure a mixture of a sodium or potassium lower-alkoxide, a lower-alkanol and 3-(chloro or bromo)-6-methyl-5-(4-pyridinyl)-2(1H)-pyridinone, and acidifying the reaction mixture to produce 3-hydroxy-6-methyl-5-(4-pyridinyl)-2(1H)-pyridinone. Sodium methoxide, methanol and 3-bromo-5-(4-pyridinyl)-2(1H)-pyridinone are preferably used in this process. The word "lower" as used herein means "alkoxides" and "alkanols" each having from one to three carbon atoms.

In another process aspect the invention resides in the process of producing 3-hydroxymethyl-6-methyl-5-(4-pyridinyl)-2(1H)-pyridinone which comprises reacting 6-methyl-5-(4-pyridinyl)-2(1H)-pyridinone with excess formaldehyde at an acidic pH, preferably about 2 to 5.

A composition aspect of the invention resides in the cardiotonic composition for increasing cardiac contractility, said composition comprising a pharmaceutically acceptable carrier and, as the active component thereof, a cardiotonically effective amount of 3-(hydroxy or hydroxymethyl)-6-methyl-5-(4-pyridinyl)-2(1H)-pyridinone or pharmaceutically acceptable acid-addition salt thereof.

A method aspect of the invention resides in the method for increasing cardiac contractility in a patient requiring such treatment which comprises administering orally or parenterally in solid or liquid dosage form to such patient a cardiotonically effective amount of 3-(hydroxy or hydroxymethyl)-6-methyl-5-(4-pyridinyl)-2(1H)-pyridinone or pharmaceutically acceptable acid-addition salt thereof.

The 3-(hydroxy or hydroxymethyl)-6-methyl-5-(4-pyridinyl)-2(1H)-pyridinone is useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to form the hydrochloride salt; however, other appropriate pharmaceutically acceptable salts within the scope of the invention are those derived from mineral acids such as sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structure of 3-(hydroxy or hydroxymethyl)-6-methyl-5-(4-pyridinyl)-2(1H)-pyridinone was assigned on the basis of evidence provided by infrared, nuclear magnetic resonance and mass spectra, by chromatographic mobilities, and, by the correspondence of calculated and found values for the elementary analyses.

The manner of making and using the instant invention will now be generally described so as to enable a person skilled in the art of pharmaceutical chemistry to make and use the same, as follows.

The reaction of 3-halo-6-methyl-5-(4-pyridinyl)-2(1H)-pyridinone with an alkali metal lower-alkoxide and a lower-alkanol to produce 3-hydroxy-6-methyl-5-(4-pyridinyl)-2(1H)-pyridinone is carried out by autoclaving the reactants, preferably using sodium methoxide, methanol and 3-bromo-6-methyl-5-(4-pyridinyl)-2(1H)-pyridinone at about 200° C., and acidifying the cooled reaction mixture or aqueous solution of its concentrate.

The reaction of 6-methyl-5-(4-pyridinyl)-2(1H)-pyridinone with excess formaldehyde at an acidic pH to produce 3-hydroxymethyl-6-methyl-5-(4-pyridinyl)-2(1H)-pyridinone is carried out by heating the reactants at about 75° to 125° C. It is preferably run using an acidic pH of about 2 to 5, a large molar excess of formaldehyde and a reaction temperature of about 90° to 110° C. The quantity of formaldehyde can vary widely provided it is in excess of said 6-methyl-5-(4-pyridinyl)-2(1H)-pyridinone. In practice, a large excess, e.g., from about 10-fold to 100-fold or greater can be used; however, as little as a 2-fold excess or less of formaldehyde can be used although the reaction time is longer. Because of its ready availability and low cost, 37% aqueous formaldehyde solution is preferred.

The intermediate 3-halo-6-methyl-5-(4-pyridinyl)-2(1H)-pyridinones are shown, as are their preparations, in Belgian Pat. No. 886,336, granted May 25, 1981, and in copending Lesher and Philion U.S. application Ser. No. 198,461, filed Oct. 20, 1980.

The intermediate 5-(4-pyridinyl)-2(1H)-pyridinone and its preparation are shown in said Belgian Pat. No. 886,336 and in U.S. Pat. No. 4,276,293, issued June 30, 1981; also, this intermediate is dislcosed and claimed in copending Lesher, Opalka and Page U.S. patent application Ser. No. 204,729, filed Nov. 6, 1980.

The following examples will further illustrate the invention without, however, limiting it thereto.

EXAMPLE 1

3-Hydroxy-6-methyl-5-(4-pyridinyl)-2(1H)-pyridinone, alternatively named 5-hydroxy-2-methyl-[3,4'-bipyridin]-6(1H)-one-A mixture containing 40 g. of 3-bromo-6-methyl-5-(4-pyridinyl)-2(1H)-pyridinone, 45 g. of sodium methoxide and 550 ml. of methanol was autoclaved at about 200° C. for twelve hours. The solvent was distilled off in vacuo and the residue was dissolved in 200 ml. of water. To the aqueous solution was added dropwise cold concentrated hydrochloric acid until neutral and the resulting solid was collected and washed with methanol. The solid was triturated with water, collected, recrystallized successively from acetone-methylene dichloride and water-ethanol. The remaining solid was dissolved in 90 ml. of hot water, the solution treated with decolorizing charcoal and filtered, and the filtrate treated with excess (3 ml.) of 6 N HCl. The mixture was concentrated to about one-third its volume, ethanol was added and the resulting precipitate was collected and dried overnite at 90° C. to yield 1.9 g. of 3-hydroxy-6-methyl-5-(4-pyridinyl)-2(1H)-pyridinone as its dihydrochloride, m.p. >300° C.

Other acid-addition salts of 3-hydroxy-6-methyl-5-(4-pyridinyl)-2(1H)-pyridinone are conveniently prepared by carefully adding to a mixture of 1 g. of 3-hydroxy-6-methyl-5-(4-pyridinyl)-2(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 3-hydroxy-6-methyl-5-(4-pyridinyl)-2(1H)-pyridinone and the appropriate acid, e.g., lactic acid or hydrochloric acid to prepare respectively the monolactate or monohydrochloride salt in aqueous solution.

EXAMPLE 2

3-Hydroxymethyl-6-methyl-5-(4-pyridinyl)-2(1H)-pyridinone, alternatively named 5-(hydroxymethyl)-2-methyl-[3,4'-bipyridin]-6(1H)-one-A mixture containing 65.8 g. of 6-methyl-5-(4-pyridinyl)-2(1H)-pyridinone, 200 ml. of 37% formaldehyde and 300 ml. of 15% aqueous sulfuric acid was heated on a steam bath for about 10 hours. The reaction mixture was neutralized with 28% aqueous ammonium hydroxide solution. The resulting precipitate was collected, treated with warm methanol and filtered. Additional product was obtained from the filtrate by evaporating it to dryness and extracting the product from the residue (product and inorganic salts) with warm methanol. The combined product (about 40 g. of crystalline material) was purified by first recrystallizing it from acetic acid-acetonitrile and then dissolving the recrystallized material in about 300 ml. of 1:1 (by volume) of chloroform:methanol, concentrating the solution to about 180 ml., filtering off the insoluble material, concentrating the filtrate in vacuo, diluting with chloroform, chilling, collecting the solid and drying it at about 75° C. over $P_2O_5$ to yield 18 g. of 3-hydroxymethyl-6-methyl-5-(4-pyridinyl)-2(1H)-pyridinone, m.p. 225°-230° C.

Acid-addition salts of 3-hydroxymethyl-6-methyl-5-(4-pyridinyl)-2(1H)-pyridinone are conveniently prepared by carefully adding to a mixture of 1 g. of 3-hydroxymethyl-6-methyl-5-(4-pyridinyl)-2(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 3-hydroxymethyl-6-methyl-5-(4-pyridinyl)-2(1H)-pyridinone and the appropriate acid, e.g., hydrochloric acid or lactic acid to prepare respectively the monohydrochloride or monolactate salt in aqueous solution.

The usefulness of 3-(hydroxy or hydroxymethyl)-6-methyl-5-(4-pyridinyl)-2(1H)-pyridinone or salt as cardiotonic agent is demonstrated by its effectiveness in standard pharmacological test procedures, for example, in causing a significant increase in the contractile force of the isolated cat or guinea pig atria and papillary muscle and in causing a significant increase in the cardiac contractile force in the anesthetized dog with low or minimal changes in heart rate and blood pressure. These test procedures are described in the U.S. Pat. No. 4,072,746, issued Feb. 7, 1980.

When tested by the above-described Isolated Cat or Guinea Pig Atria and Papillary Muscle Procedures, 3-(hydroxy or hydroxymethyl)-6-methyl-5-(4-pyridinyl)-2(1H)-pyridinone, when tested at doses of 1, 3, 10, 30 or 100 μg./ml., was found to cause significant increase, that is, greater than 25% or 30% in papillary muscle force and a significant increase, that is, greater than 25% or 30% in right atrial force, while causing only a low percentage increase (about one-third or less than the percentage increase in right atrial or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. Moreover, the 6-methyl compounds of Examples 1 and 2 unexpectedly were found to be markedly more active as cardiotonics in comparison with the corresponding prior art 6-desmethyl compounds, that is, Examples 1 and 2 of U.S. Pat. No. 4,225,601, issued Sept. 30, 1980, when tested by said cat or guinea pig atria and papillary muscle procedure. For example, the percentage increases in cat papillary muscle force and right atrial force for 3-hydroxy-6-methyl-5-(4-pyridinyl)-2(1H)-pyridinone, Example 1 herein, were found to be 73% and 112% respectively when tested at 1 μg./ml. compared with corresponding respective increases of 56% and 38% for prior art 3-hydroxy-5-(4-pyridinyl)-2(1H)-pyridinone at 100 μg./ml., that is, at one hundred times the dose. Similarly, the percentage increase in guinea pig papillary muscle force for 3-hydroxymethyl-6-methyl-5-(4-pyridinyl)-2(1H)-pyridinone, Example 2 herein, was found to be 98% at 10 μg./ml. compared with cat papillary muscle force percentage increase of 54% at 100 μg./ml. for prior art 3-hydroxymethyl-5-(4-pyridinyl)-2(1H)-pyridinone, that is, at ten times the dose.

The present invention includes within its scope a cardiotonic composition for increasing cardiac contractility, said composition comprising a pharmaceutically acceptable carrier and, as the active component thereof, the cardiotonic 3-(hydroxy or hydroxymethyl)-6-methyl-5(4-pyridinyl)-2(1H)-pyridinone or pharmaceutically acceptable acid-addition salt thereof. The invention also includes within its scope the method for increasing cardiac contractility in a patient requiring such treatment which comprises administering to such patient a cardiotonically effective amount of said 3-(hydroxy or hydroxymethyl)-6-methyl-5-(4-pyridinyl)-2(1H)-pyridinone or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3-(Hydroxy or hydroxymethyl)-6-methyl-5-(4-pyridinyl)-2(1H)-pyridinone or pharmaceutically acceptable acid-addition salt thereof.

2. 3-Hydroxy-6-methyl-5-(4-pyridinyl)-2(1H)-pyridinone or pharmaceutically acceptable acid-addition salt thereof.

3. 3-Hydroxymethyl-6-methyl-5-(4-pyridinyl)-2(1H)-pyridinone or pharmaceutically acceptable acid-addition salt thereof.

4. A cardiotonic composition for increasing cardiac contractility, said composition comprising a pharmaceutically acceptable inert carrier and, as the active component thereof, a cardiotonically effective amount of 3-(hydroxy or hydroxymethyl)-6-methyl-5-(4-pyridinyl)-2(1H)-pyridinone or pharmaceutically acceptable acid-addition salt thereof.

5. A composition according to claim 4 where the active component is 3-hydroxy-6-methyl-5-(4-pyridinyl)-2(1H)-pyridinone.

6. A composition according to claim 4 where the active component is 3-hyroxymethyl-6-methyl-5-(4-pyridinyl)-2(1H)-pyridinone.

7. The method for increasing cardiac contractility in a patient requiring such treatment which comprises administering orally or parenterally in a solid or liquid dosage form to such patient a cardiotonically effective amount of 3-(hydroxy or hydroxymethyl)-6-methyl-5-(4-pyridinyl)-2(1H)-pyridinone or pharmaceutically acceptable acid-acceptable salt thereof.

* * * * *